United States Patent
Shi et al.

(10) Patent No.: US 10,950,328 B2
(45) Date of Patent: Mar. 16, 2021

(54) METHOD, APPARATUS AND SYSTEM FOR DETECTING STRUCTURAL VARIATIONS

(71) Applicant: BEIJING BAIDU NETCOM SCIENCE AND TECHNOLOGY CO., LTD., Beijing (CN)

(72) Inventors: Ziye Shi, Beijing (CN); Shan He, Beijing (CN); Dongze Xu, Beijing (CN); Faen Zhang, Beijing (CN); Lizhi Wu, Beijing (CN)

(73) Assignee: BEIJING BAIDU NETCOM SCIENCE AND TECHNOLOGY CO., LTD., Beijing (CN)

( * ) Notice: Subject to any disclaimer, the term of this patent is extended or adjusted under 35 U.S.C. 154(b) by 825 days.

(21) Appl. No.: 15/495,307

(22) Filed: Apr. 24, 2017

(65) Prior Publication Data

US 2018/0082015 A1    Mar. 22, 2018

(30) Foreign Application Priority Data

Sep. 18, 2016  (CN) .......................... 201610829652.5

(51) Int. Cl.
*G16B 50/00* (2019.01)
*G01N 35/00* (2006.01)

(52) U.S. Cl.
CPC ......... *G16B 50/00* (2019.02); *G01N 35/0092* (2013.01); *G01N 35/00871* (2013.01); *G01N 2035/0094* (2013.01)

(58) Field of Classification Search
None
See application file for complete search history.

(56) References Cited

U.S. PATENT DOCUMENTS

2015/0331724 A1  11/2015  Sahu

FOREIGN PATENT DOCUMENTS

| CN | 101560564 A | 10/2009 |
|----|-------------|---------|
| CN | 102984080 A | 3/2013  |
| CN | 104615498 A | 5/2015  |
| CN | 105573827 A | 5/2016  |
| JP | 2015197899 A | 11/2015 |
| WO | 2015085147 A1 | 6/2015 |

OTHER PUBLICATIONS

Illumina MiSeq System User Guide Illumina Inc. (Year: 2013).*
Yap et al. Parallel Computation in Biological Sequence Analysis IEEE Transactions on Parallel and Distributed Systems vol. 9, pp. 283-294 (Year: 1998).*
First office action and search report from CN app. No. 201610829652.5, dated Jan. 11, 2018, with machine English translation from Google Translate.
Second Office Action and supplementary search report from CN app. No. 201610829652.5, dated Feb. 27, 2018, with English translation from Global Dossier.
Notice of Reasons for Refusal from JP app. No. 2017-097973, dated May 8, 2018, with English translation from Global Dossier.
Decision to Grant a Patent from JP app. No. 2017-097973, dated Dec. 4, 2018, with English translation from Global Dossier.
Decision of Refusal from JP app. No. 2017-097973, dated Aug. 7, 2018, with English translation from Global Dossier.
Notification of Reason for Refusal from KR app. No. 10-2017-0054130, dated Nov. 19, 2018, with English translation from Global Dossier.
Grant of Patent from KR app. No. 10-2017-0054130, dated May 28, 2019, with English translation from Global Dossier.

* cited by examiner

*Primary Examiner* — John S Brusca
(74) *Attorney, Agent, or Firm* — Ladas & Parry, LLP

(57) ABSTRACT

A method, apparatus and system for detecting structural variations is provided. A management apparatus divides a test sequence according to loci of chromosomes to obtain at least two portions of detection tasks, sends respective detection tasks to respective detection apparatuses and activates the respective detection tasks; detects detection task completion situations of detection apparatuses and determines whether the number of uncompleted tasks is reduced to a preset proportion threshold of a total number of tasks; when the number is reduced to a preset proportion threshold of the total number of tasks, the management apparatus sends, to detection apparatuses that have not yet completed detection tasks, an instruction message to kill uncompleted detection tasks; the management apparatus further divides the uncompleted detection tasks into at least two portions, sends respective detection tasks to respective detection apparatuses, and activates said respective detection apparatuses to continue to perform detection of structural variations.

11 Claims, 4 Drawing Sheets

METHOD, APPARATUS AND SYSTEM FOR DETECTING STRUCTURAL VARIATIONS

The present application claims the priority of Chinese Patent Application No. 201610829652.5, filed on Sep. 18, 2016, the content of which is incorporated herein by reference.

FIELD OF THE DISCLOSURE

The present disclosure relates to the technical field of gene detection, and particularly to a method, apparatus and system for detecting structural variations.

BACKGROUND OF THE DISCLOSURE

In current human being whole-genome re-sequencing, structural variation detection needs to be performed for massive raw data to perform data analysis.

As the amount of current data increases, a scheme that may be supported comprises a non-concurrent scheme in the current structural variation detection. This scheme is adapted to perform detection for all test sequences in a single-unit single-process manner. In this scheme, computer resources are not used sufficiently, and the testing duration is very long. To reduce the testing duration, the prior art makes improvements to the non-concurrent scheme and proposes a concurrent scheme for detecting structural variations. In this scheme, the test sequence is segmented according to chromosomes. Upon processing, each apparatus may process chromosomes in a designated chromosome segment. As such, processing may be executed concurrently between multiple segments of chromosomes, and one chromosome is processed with one process. To further use computer resources, in the prior art there is further proposed a simple concurrent calculation scheme in the chromosomes. According to the scheme, the test sequence is divided according to chromosomes, then each chromosome is sliced into N portions according to loci, and each portion activates a process for concurrent execution.

However, a processing duration varies with different loci of chromosomes, and a processing duration between segments also varies. This causes allocation of concurrent tasks uneven: some concurrent tasks are completed very quickly, and some require a very long period of time. As a result, there are idle computer resources that are not used sufficiently, and the testing duration of the whole test sequence is relatively long.

SUMMARY OF THE DISCLOSURE

The present disclosure provides a method, apparatus and system for detecting structural variations, for sufficiently using computer resources and shortening the testing duration of the whole test sequence.

The present disclosure provides a method of detecting structural variations, the method comprising:

a management apparatus divides a test sequence according to loci of chromosomes to obtain at least two portions of detection tasks;

the management apparatus sends respective detection tasks to respective detection apparatuses and activates the respective detection tasks;

the management apparatus detects detection task completion situations of at least two detection apparatuses and determines whether the number of uncompleted tasks is reduced to a preset proportion threshold of a total number of tasks;

when the number of uncompleted tasks is reduced to the preset proportion threshold of the total number of tasks, the management apparatus sends, to detection apparatuses that have not yet completed detection tasks, an instruction message to kill uncompleted detection tasks;

the management apparatus further divides the uncompleted detection tasks into at least two portions, sends respective detection tasks to respective detection apparatuses, and activates said respective detection apparatuses to continue to perform detection of structural variations.

Further optionally, in the above method, the management apparatus dividing a test sequence according to loci of chromosomes to obtain at least two portions of detection tasks specifically comprises:

the management apparatus divides the test sequence according to chromosomes;

the management apparatus divides all chromosomes after the division according to loci to obtain at least two portions of detection tasks.

Further optionally, in the above method, the management apparatus dividing all chromosomes after the division according to loci to obtain at least two portions of detection tasks specifically comprises: according to the number of detection apparatuses included in the structural variation detection system and the number of cores of each detection apparatus, the management apparatus divides all chromosomes after the division according to loci to obtain at least two portions of detection tasks; and the number of portions of the at least two portions of detection tasks is equal to an integer multiple of a product of the number of detection apparatuses and the number of cores of each computer.

Further optionally, in the above method, when the number of uncompleted tasks is reduced to the original preset proportion threshold, and after the management apparatus sends, to detection apparatuses that have not yet completed detection tasks, an instruction message to kill uncompleted detection tasks, the method further comprises:

receiving a listing of killed detection tasks which are sent by the detection apparatus.

Further optionally, in the above method, when the management apparatus detects completion of detection tasks of respective detection apparatuses, the method may further comprise the following steps:

the management apparatus receives a detection result file which is sent by each detection apparatus and with respect to a corresponding detection task;

the management apparatus merges the received detection result files.

The present disclosure provides a method of detecting structural variations, the method comprising:

a detection apparatus receives a detection task sent by a management apparatus;

the detection apparatus receives an instruction message sent by the management apparatus to activate the detection task;

the detection apparatus, according to the instruction message to activate the detection task, simultaneously activates detection with respect to corresponding detection tasks together with other detection apparatuses;

when the management apparatus detects that the number of uncompleted tasks is reduced to a preset proportion threshold of the total number of tasks, and when the current detection apparatuses have not completed the detection, the detection apparatus receives an instruction message which is sent by the management apparatus and instructs to kill the uncompleted detection tasks;

the detection apparatus, according to the instruction message to kill the uncompleted detection tasks, kills the uncompleted detection tasks so that the management apparatus further divides the uncompleted detection task into at least two portions, sends respective detection tasks to respective detection apparatuses, and activates the detection apparatuses to continue to perform structural variation detection.

Further optionally, in the above method, after the detection apparatus receives an instruction message which is sent by the management apparatus and instructs to kill the uncompleted detection tasks and before the detection apparatus, according to the instruction message to kill the uncompleted detection tasks, kills the uncompleted detection tasks, the method further comprises:

the detection apparatus judges whether a maximum interval of loci values in chromosome segments corresponding to the uncompleted detection tasks is greater than or equal to a preset loci interval;

the detection apparatus determines that the maximum interval of loci values in chromosome segments corresponding to the uncompleted detection tasks is greater than or equal to the preset loci interval.

Further optionally, in the above method, when the maximum interval of loci values in chromosome segments corresponding to the uncompleted detection tasks is smaller than the preset loci interval, the method comprises:

the detection apparatus does not kill uncompleted processes and monitors the process of structural variation detection of the detection task until the detection is completed;

the detection apparatus sends a detection result file of a corresponding detection task to the management apparatus.

The present disclosure further provides a management apparatus of detecting the structural variations, the management apparatus comprising:

a task dividing module configured to divide a test sequence according to loci of chromosomes to obtain at least two portions of detection tasks;

a task sending and activating modules configured to send respective detection tasks to respective detection apparatuses and activate the respective detection tasks;

a task detection module configured to detect detection task completion situations of at least two detection apparatuses and determine whether the number of uncompleted tasks is reduced to a preset proportion threshold of a total number of tasks;

a task processing module configured to send, to detection apparatuses that have not yet completed detection tasks, an instruction message to kill uncompleted detection tasks when the number of uncompleted tasks is reduced to the preset proportion threshold of the total number of tasks;

the task dividing module further configured to divide the uncompleted detection tasks into at least two portions;

the task sending and activating module further configured to send respective detection tasks to respective detection apparatuses, and activate said respective detection apparatuses to continue to perform detection of structural variations.

Further optionally, in the aforesaid apparatus, the task dividing module is specifically configured to:

divide the test sequence according to chromosomes; and
divide all chromosomes after the division according to loci to obtain at least two portions of detection tasks.

Further optionally, in the aforesaid apparatus, the task dividing module is specifically configured in a way that according to the number of detection apparatuses included in the structural variation detection system and the number of cores of each detection apparatus in the structural variation detection system, divides all chromosomes after the division according to loci to obtain at least two portions of detection tasks; and the number of portions of the at least two portions of detection tasks is equal to an integer multiple of a product of the number of detection apparatuses and the number of cores of each computer.

Further optionally, the aforesaid apparatus further comprises:

a receiving module configured to receive a listing of killed detection tasks which are sent by the detection apparatuses.

Further optionally, the apparatus further comprises a merging module;

the receiving module is further configured to receive a detection result file which is sent by each detection apparatus and with respect to a corresponding detection task when the detection tasks of detection apparatuses have been detected completed;

the merging module is configured to merge the received detection result files.

The present disclosure further provides a detection apparatus of detecting structural variations, the detection apparatus comprising:

a receiving module configured to receive a detection task sent by a management apparatus;

the receiving module further configured to receive an instruction message sent by the management apparatus to activate the detection task;

a task activating module configured to, according to the instruction message to activate the detection task, simultaneously activate detection with respect to corresponding detection tasks together with other detection apparatuses;

the receiving module is further configured to, when the management apparatus detects that the number of uncompleted tasks is reduced to a preset proportion threshold of the total number of tasks, and when the current detection apparatuses have not completed the detection, receive an instruction message which is sent by the management apparatus and instructs to kill the uncompleted detection tasks;

a task processing module configured to, according to the instruction message to kill the uncompleted detection tasks, kill the uncompleted detection tasks so that the management apparatus further divides the uncompleted detection task into at least two portions, sends respective detection tasks to respective detection apparatuses, and activates the detection apparatuses to continue to perform structural variation detection.

Further optionally, the aforesaid apparatus further comprises: a task detection module is configured to judge whether a maximum interval of loci values in chromosome segments corresponding to the uncompleted detection tasks is greater than or equal to a preset loci interval; and determine that the maximum interval of loci values in chromosome segments corresponding to the uncompleted detection tasks is greater than or equal to the preset loci interval.

Further optionally, the aforesaid apparatus further comprise a transmitting module;

the task processing module is further configured not to kill uncompleted processes when the maximum interval of loci values in chromosome segments corresponding to the uncompleted detection tasks is smaller than the preset loci interval, and configured to monitor the process of structural variation detection of the detection task until the detection is completed;

the transmitting module is configured to transmit a detection result file of a corresponding detection task to the management apparatus.

The present disclosure further provides a structural variation detection system, the system comprising: a management apparatus for detecting structural variations and at least two detection apparatuses for detecting structural variations, wherein the management apparatus for detecting structural variations is communicatively connected with the detection apparatuses for detecting structural variations;

The management apparatus for detecting structural variations employs the management apparatus for detecting structural variations; the detection apparatuses for detecting structural variations employ the detection apparatuses for detecting structural variations.

According to the method and apparatuses for detecting structural variations in the present disclosure, the management apparatus divides the test sequence according to loci of the chromosomes to obtain at least two portions of detection tasks; sends detection tasks to the detection apparatuses and activates the detection tasks; detects detection task completion situations of at least two detection apparatuses and determines whether the number of uncompleted tasks is reduced to a preset proportion threshold of a total number of tasks; when the number of uncompleted tasks is reduced to the preset proportion threshold of the total number of tasks, sends, to detection apparatuses that have not yet completed detection tasks, an instruction message to kill uncompleted detection tasks; further divides the uncompleted detection tasks into at least two portions, sends respective detection tasks to respective detection apparatuses, and activates said respective detection apparatuses to continue to perform detection of structural variations. With the technical solutions of the present disclosure being employed, chromosome segments corresponding to the uncompleted process in each round of structural variation detection is regarded as a test sequence again to repeatedly and iteratively execute the above steps, to sufficiently use the computer resources, quicken the detection process of structural variations of the whole test sequence, shorten the detection duration of the structural variations of the whole test sequence, and improve the detection efficiency.

DETAILED DESCRIPTION OF PREFERRED EMBODIMENTS

The present disclosure will be described in detail in conjunction with figures and specific embodiments to make objectives, technical solutions and advantages of the present disclosure more apparent.

Figure 1:
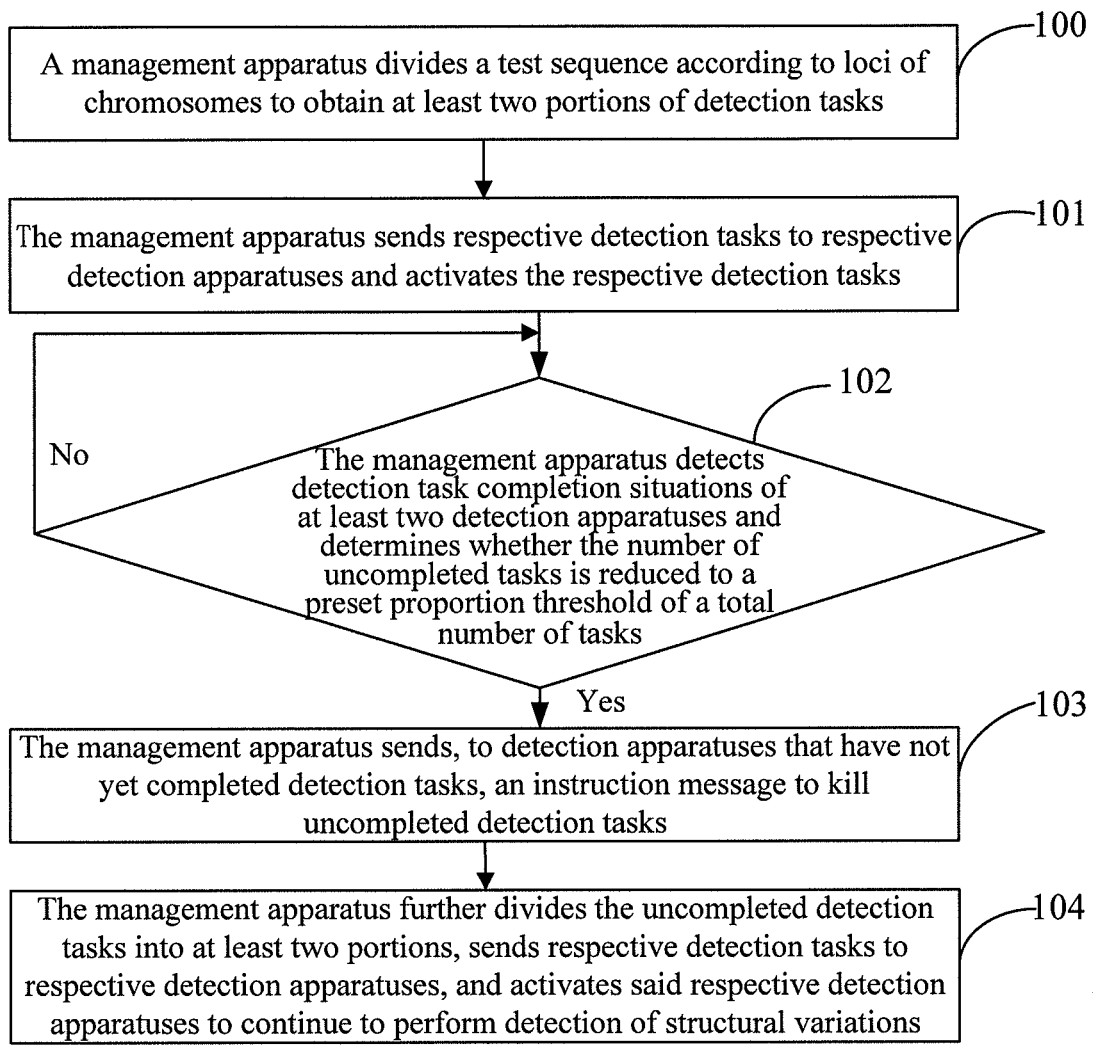
FIG. 1 is a flow chart of Embodiment 1 of a method of detecting structural variations according to the present disclosure.

FIG. 1 is a flow chart of Embodiment 1 of a method of detecting structural variations according to the present disclosure. As shown in FIG. 1, the method of detecting structural variations according to the present embodiment may specifically comprise the following steps:

100: a management apparatus divides a test sequence according to loci of chromosomes to obtain at least two portions of detection tasks;

101: the management apparatus sends respective detection tasks to respective detection apparatuses and activates the respective detection tasks;

For example, the detection tasks may be specifically activated by sending the detection apparatuses an instruction message indicative of activating the detection tasks.

102: The management apparatus detects detection task completion situations of at least two detection apparatuses and determines whether the number of uncompleted tasks is reduced to a preset proportion threshold of a total number of tasks; when the number of uncompleted tasks is reduced to the preset proportion threshold of the total number of tasks, executes step 103; otherwise, returns to step 102 to continue detection;

103: the management apparatus sends, to detection apparatuses that have not yet completed detection tasks, an instruction message to kill uncompleted detection tasks; executes step 104;

104: the management apparatus further divides the uncompleted detection tasks into at least two portions, sends respective detection tasks to respective detection apparatuses, and activates said respective detection apparatuses to continue to perform detection of structural variations.

The method for detecting structural variations in the present embodiment is applied to a structural variation detecting system. The structural variation detecting system may comprise a management apparatus for detecting structural variations (hereinafter referred to as "management apparatus") and at least two detection apparatuses for detecting structural variations (hereinafter referred to "detection apparatuses"). The management apparatus manages said at least two detection apparatuses to manage said at least two detection apparatuses to perform detection tasks.

The method for detecting structural variations in the present embodiment is applied to human being whole genome re-sequencing. The test sequence of the present embodiment is comprised of many chromosomes. First, the management apparatus divides the test sequence according to loci of the chromosomes to obtain at least two chromosome segments, and each chromosome segment serves as a detection task. For example, each chromosome segment resulting from the division has an equal length, that is, an interval of loci values in each chromosome segment resulting from the division is equal. Upon structural variation detection, each detection task may be assigned in at least one detection apparatus which activates one detection task correspondingly. As such, at least two portions of detection tasks may be activated simultaneously to concurrently perform structural variation detection; then, the management apparatus detects detection task completion situations of at least two detection apparatuses and determines whether the number of uncompleted tasks is reduced to a preset proportion threshold of a total number of tasks; when the number of uncompleted tasks is reduced to the preset proportion threshold of the total number of tasks, executes step 103; otherwise, returns to step 102 to continue detection; the preset proportion threshold in the present embodiment may be set according to actual needs, and it specifically may be any proportion between 0 and 1, for example, ½, or ⅓ or any other proportion value. When the number of uncompleted tasks is reduced to the preset proportion threshold of the total number of tasks, detection will be continued. Otherwise, when the number of uncompleted tasks is reduced to the preset proportion threshold of the total number of tasks, the management apparatus sends, to detection apparatuses that have not yet completed detection tasks, an instruction message to kill uncompleted detection tasks; the management apparatus further divides the uncompleted detection tasks into at least two portions, sends respective detection tasks to respective detection apparatuses, and activates said respective detection apparatuses to continue to perform detection of structural variations. That is to say, when the number of uncompleted tasks is reduced to the preset proportion threshold of the total number of tasks, partial processes have already completed detection and still partial processes have not yet completed detection. This causes allocation of detection tasks uneven, and in the detection apparatuses that have completed detection there are still idle computer resources that are not used sufficiently. Hence, in the present embodiment, the uncompleted detection tasks, as a test sequence, continues to be further divided into at least two portions according to loci of chromosomes, respective detection tasks are sent to respective detection apparatuses, and said respective detection apparatuses are activated to continue to perform detection of structural variations, that is, the above steps are executed repeatedly and iteratively to sufficiently use the computer resources, quicken the structural variation detection process, shorten the detection duration of the structural variations, and improve the detection efficiency.

According to the method for detecting structural variations in the present embodiment, the management apparatus divides the test sequence according to loci of the chromosomes to obtain at least two portions of detection tasks; sends detection tasks to the detection apparatuses and activates the detection tasks; detects detection task completion situations of at least two detection apparatuses and determines whether the number of uncompleted tasks is reduced to a preset proportion threshold of a total number of tasks; when the number of uncompleted tasks is reduced to the preset proportion threshold of the total number of tasks, sends, to detection apparatuses that have not yet completed detection tasks, an instruction message to kill uncompleted detection tasks; further divides the uncompleted detection tasks into at least two portions, sends respective detection tasks to respective detection apparatuses, and activates said respective detection apparatuses to continue to perform detection of structural variations. With the technical solution of the present embodiment being employed, chromosomes corresponding to the uncompleted process in each round of structural variation detection is regarded as a test sequence again to repeatedly and iteratively execute the above steps, to sufficiently use the computer resources, quicken the detection process of structural variations of the whole test sequence, shorten the detection duration of the structural variations of the whole test sequence, and improve the detection efficiency.

Further optionally, on the basis of the technical solution of the above embodiment, the step 100 "a management apparatus divides a test sequence according to loci of chromosomes to obtain at least two portions of detection tasks" in the above embodiment specifically comprises:

(a1) the management apparatus divides the test sequence according to chromosomes;

(a2) the management apparatus divides all chromosomes after the division according to loci to obtain at least two portions of detection tasks.

The test sequence is comprised of chromosomes, and chromosomes further comprise many loci. In the technical solution of the present embodiment, first the management apparatus divides the test sequence according to chromosomes, and then divides all chromosomes after the division according to the loci to obtain at least two chromosome segments. Preferably, the chromosome segments resulting from the division are equal.

Preferably, the step (a2) "the management apparatus divides all chromosomes after the division according to loci to obtain at least two portions of detection tasks" in the above embodiment specifically comprises: according to the number of detection apparatuses included in the structural variation detection system and the number of cores of each detection apparatus, the management apparatus divides all chromosomes after the division according to loci to obtain at least two portions of detection tasks; and the number of portions of the at least two portions of detection tasks is equal to an integer multiple of a product of the number of detection apparatuses and the number of cores of each computer.

That is to say, it is feasible to, according to the number of detection apparatuses included in the structural variation detection system and the number of cores of each detection apparatus, divide all chromosomes after the division according to loci so that the number of divided detection tasks is right equal to an integer multiple of a product of the number of detection apparatuses and the number of cores of each computer. As such, when the structural variation detection is performed, it is feasible to ensure the number of detection tasks assigned to each detection apparatus to be equal, which may sufficiently use the computer resources, can ensure balance of the structural variation detection tasks to a maximum degree, and thereby shorten the detection duration of the whole test sequence, and improve the detection efficiency. Furthermore, in the method of detecting structural variations in the present embodiment, it is further feasible to, according to the number of detection apparatuses included in the structural variation detection system and the number of cores of each detection apparatus, flexibly change the number of detection tasks and exhibit a strong expandability capability.

Further optionally, on the basis of the technical solution of the above embodiment, after the step 103 "when the number of uncompleted tasks is reduced to the original preset proportion threshold, the management apparatus sends, to detection apparatuses that have not yet completed detection tasks, an instruction message to kill uncompleted detection tasks", the method further comprises: receiving a listing of killed detection tasks which are sent by the detection apparatus.

That is to say, after the management apparatus sends the detection apparatuses an instruction message to kill uncompleted detection tasks, and the detection apparatuses receive the instruction message, it is feasible to, according to the instruction message, detect whether it is necessary to kill the detection task, and kill the detection task if it is necessary. As such, the management apparatus may, according to the detection task sent to the detection apparatus then, regard the detection task as a new test sequence, and continue to divide according to step 100, and continue to perform iterative detection according to steps 101-103.

After the detection apparatus receives the instruction message to kill the detection task, a condition for detecting whether it is necessary to kill the detection task may specifically be judging whether a maximum interval of loci values in chromosome segments corresponding to the uncompleted detection tasks is greater than or equal to a preset loci interval; if yes, it is necessary to kill the detection task; if the maximum interval of loci values in chromosome segments corresponding to the uncompleted detection tasks is smaller than a preset loci interval, the detection apparatus may believe at this time that the preset loci interval is a segment with a minimum unit in the chromosome segments, and cannot be further divided. If the maximum interval of loci values in chromosome segments corresponding to the uncompleted detection tasks is smaller than a preset loci interval, it is unnecessary at this time to kill the detection task, but monitor completion of execution of the detection task.

In addition, preferably, the detection apparatus may send the management apparatus a listing of detection tasks to be killed. At this time, the management apparatus may, according to the detection task which is reported by the detection apparatus and to be killed, continue to perform iterative detection according to the steps 100-103.

Further optionally, on the basis of the technical solution of the above embodiment, when the management apparatus detects completion of detection tasks of respective detection apparatuses, the method may further comprise the following steps:

(b1) the management apparatus receives a detection result file which is sent by each detection apparatus and with respect to a corresponding detection task;

(b2) the management apparatus merges the received detection result files.

After each detection apparatus completes the detection task sent thereto, it generates a corresponding detection result file. After completing the detection task sent to it, the detection apparatus generates a corresponding detection result file, and sends the detection result file to the management apparatus. As such, the management apparatus merges all detection result files generated by respective detection apparatuses, as a final detection result file of the test sequence.

With the technical solution of the present embodiment being employed, the uncompleted detection tasks in each round of structural variation detection is considered as a segment of test sequence again to repeatedly and iteratively execute the above steps, to sufficiently use the computer resources, quicken the detection process of structural variations of the whole test sequence, shorten the detection duration of the structural variations of the whole test sequence, and improve the detection efficiency.

Figure 2:
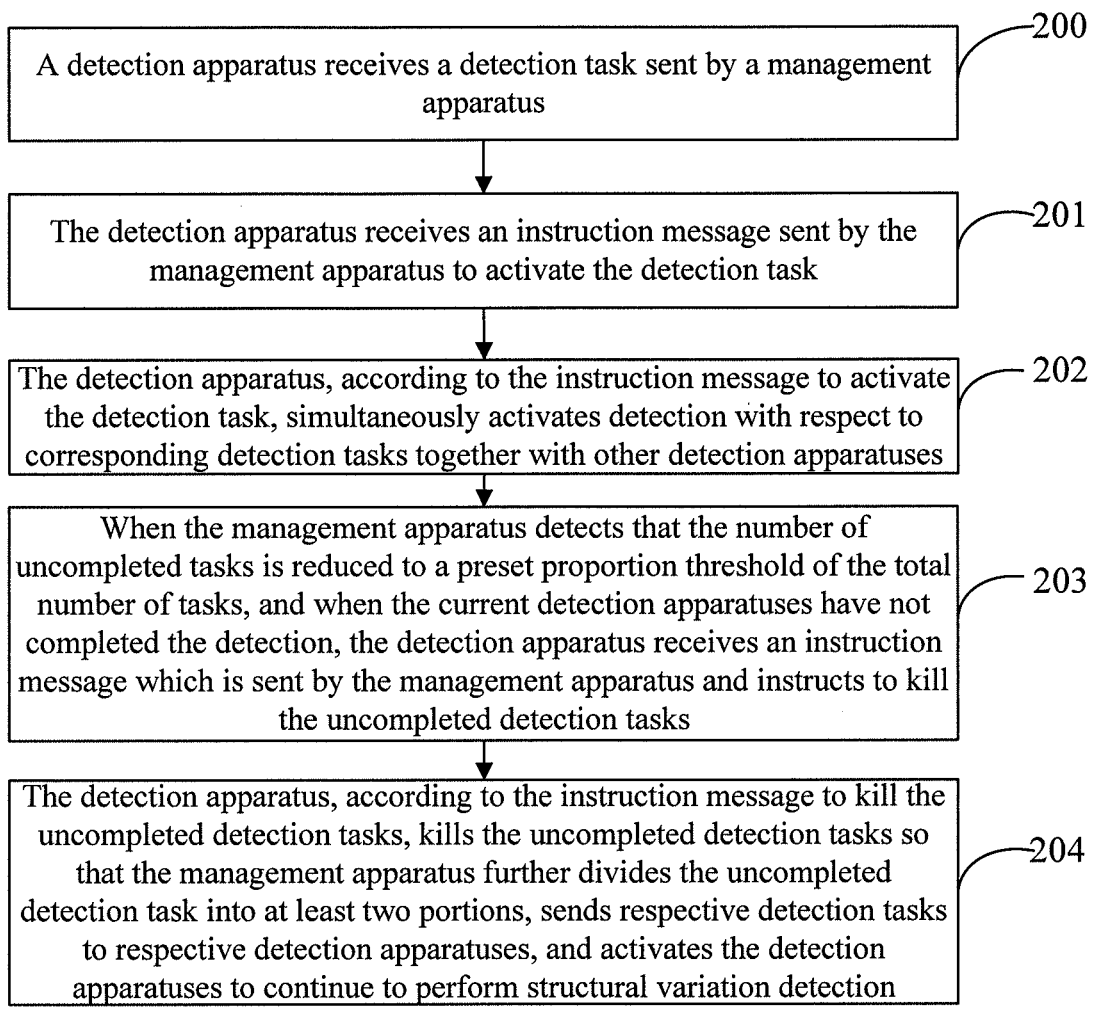
FIG. 2 is a flow chart of Embodiment 2 of a method of detecting structural variations according to the present disclosure.

FIG. 2 is a flow chart of Embodiment 2 of a method of detecting structural variations according to the present disclosure. As shown in FIG. 2, the method of detecting structural variations according to the present embodiment may specifically comprise the following steps:

200: a detection apparatus receives a detection task sent by a management apparatus;

201: the detection apparatus receives an instruction message sent by the management apparatus to activate the detection task;

202: the detection apparatus, according to the instruction message to activate the detection task, simultaneously activates detection with respect to corresponding detection tasks together with other detection apparatuses;

203: when the management apparatus detects that the number of uncompleted tasks is reduced to a preset proportion threshold of the total number of tasks, and when the current detection apparatuses have not completed the detection, the detection apparatus receives an instruction message which is sent by the management apparatus and instructs to kill the uncompleted detection tasks.

204: the detection apparatus, according to the instruction message to kill the uncompleted detection tasks, kills the uncompleted detection tasks so that the management apparatus further divides the uncompleted detection task into at least two portions, sends respective detection tasks to respective detection apparatuses, and activates the detection apparatuses to continue to perform structural variation detection.

The method of detecting structural variation in the present embodiment is applied to the same scenario as the embodiment as shown in FIG. 1. The embodiment as shown in FIG. 1 is applied on a management apparatus side of the structural variation detection system. Different from the embodiment as shown in FIG. 1, the technical solution of the present embodiment is applied to a detection apparatus side of the structural variation detection system. In the present embodiment, the technical solution of the present disclosure is described by taking the current detection apparatus has not yet completed detection when the management apparatus detects that the number of uncompleted tasks is reduced to a preset proportion threshold of the total number of tasks. When the management apparatus detects that the number of uncompleted tasks is reduced to a preset proportion threshold of the total number of tasks, and when the current detection apparatus completes the detection, the current detection apparatus reports a detection result to the management apparatus. Since the current detection apparatus has already completed the detection, there is no detection task to be killed. The procedure of implementing the method for detecting structural variations in the present embodiment is identical with the principle for implementing the method of detecting the structural variations on the management apparatus side. For details, reference may be made to the disclosure of the method of detecting the structural variations on the management apparatus side, and no detailed depictions are presented here.

According to the method of detecting the structural variations in the present embodiment, the detection apparatus receives the detection task sent by the management apparatus; receives the instruction message sent by the management apparatus to activate the detection task; according to the instruction message to activate the detection task, simultaneously activates detection with respect to corresponding detection tasks together with other detection apparatuses; when the management apparatus detects that the number of uncompleted tasks is reduced to a preset proportion threshold of the total number of tasks, and when the current detection apparatuses do not complete the detection, the detection apparatus receives an instruction message which is sent by the management apparatus and instructs to kill the uncompleted detection tasks; according to the instruction message to kill the uncompleted detection tasks, kills the uncompleted detection tasks so that the management apparatus further divides the uncompleted detection task into at least two portions, sends respective detection tasks to respective detection apparatuses, and activates the detection apparatuses to continue to perform structural variation detection. With the technical solution being employed, the uncompleted detection tasks in each round of structural variation detection is considered as a segment of test sequence again to repeatedly and iteratively execute the above steps, to sufficiently use the computer resources, quicken the detection process of structural variations of the whole test sequence, shorten the detection duration of the structural variations of the whole test sequence, and improve the detection efficiency.

Further optionally, on the basis of the technical solution of the above embodiment, after the step 203 "the detection apparatus receives an instruction message which is sent by the management apparatus and instructs to kill the uncompleted detection tasks" and before step 204 "the detection apparatus, according to the instruction message to kill the uncompleted detection tasks, kills the uncompleted detection tasks", the method may further comprise the following steps:

(c1) the detection apparatus judges whether a maximum interval of loci values in chromosome segments corresponding to the uncompleted detection tasks is greater than or equal to a preset loci interval;

(c2) the detection apparatus determines that the maximum interval of loci values in chromosome segments corresponding to the uncompleted detection tasks is greater than or equal to the preset loci interval.

Further optionally, on the basis of the technical solution of the above embodiment, when the maximum interval of loci values in chromosome segments corresponding to the uncompleted detection tasks is smaller than the preset loci interval, the method may comprise the following steps:

(d1) the detection apparatus does not kill uncompleted processes and monitors the process of structural variation detection of the detection task until the detection is completed;

(d2) the detection apparatus sends a detection result file of a corresponding detection task to the management apparatus.

At this time, the detection apparatus may believe that the preset loci interval is the segment with the smallest unit among the chromosome segments, and cannot be further divided. If the maximum interval of loci values in chromosome segments corresponding to the uncompleted detection tasks is smaller than the preset loci interval, it is unnecessary at this time to kill the detection task, but monitor completion of execution of the detection task.

The method for detecting structural variations in the present embodiment is identical with the implementation principle on the management apparatus side of the structural variation detection system. For details, reference may be made to the method of detecting the structural variations on the management apparatus side of the structural variation detection system in the above embodiment, and no detailed depictions are presented here.

Figure 3:
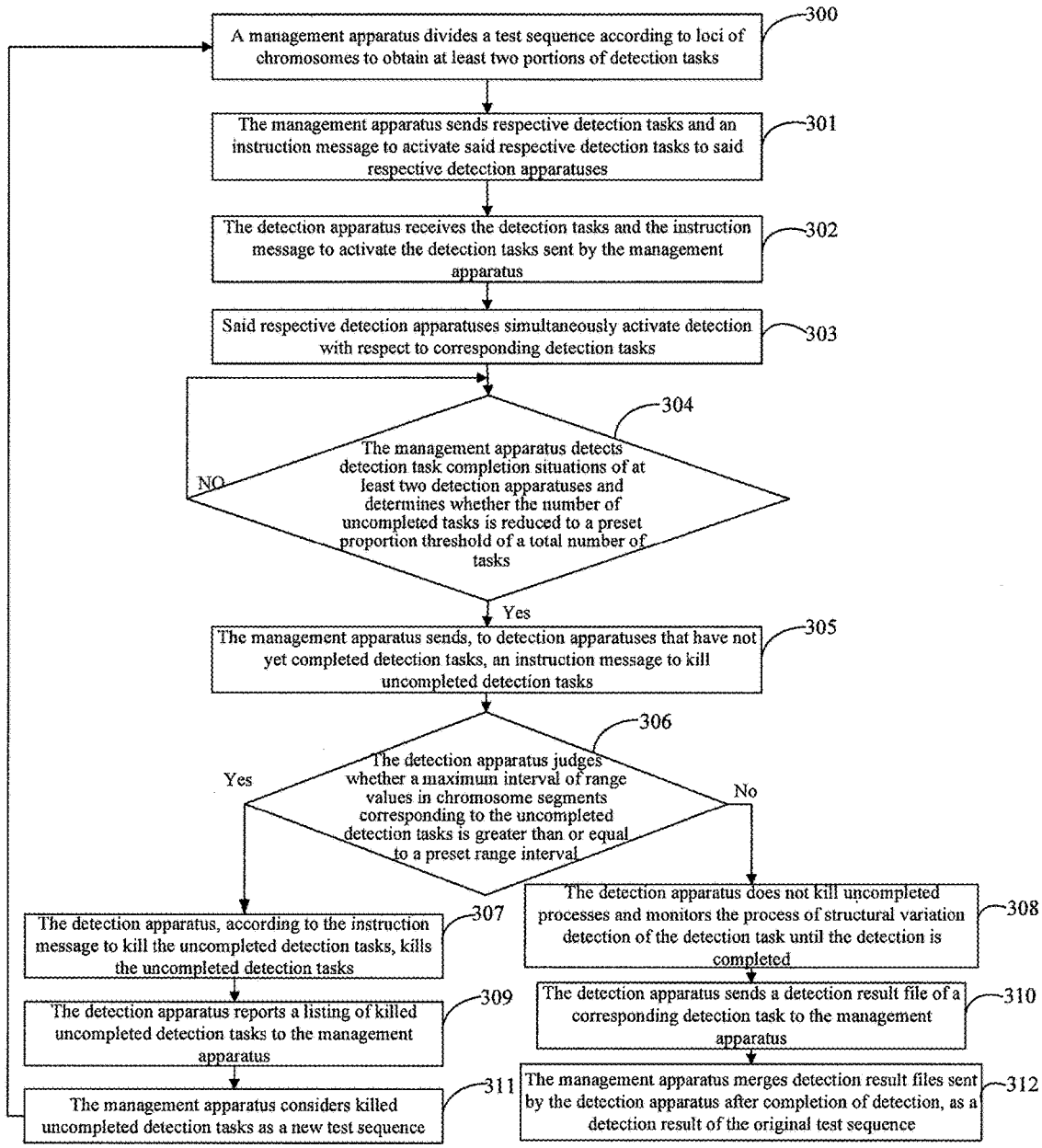
FIG. 3 is a flow chart of Embodiment 3 of a method of detecting structural variations according to the present disclosure.

FIG. 3 is a flow chart of Embodiment 3 of a method of detecting structural variations according to the present disclosure. As shown in FIG. 3, the method of detecting structural variations according to the present embodiment may specifically comprise the following steps:

300: a management apparatus divides a test sequence according to loci of chromosomes to obtain at least two portions of detection tasks;

301: the management apparatus sends respective detection tasks and an instruction message to activate said respective detection tasks to said respective detection apparatuses;

302: the detection apparatus receives the detection tasks and the instruction message to activate the detection tasks sent by the management apparatus;

303: said respective detection apparatuses simultaneously activate detection with respect to corresponding detection tasks;

That is, said respective detection apparatuses concurrently perform detection with respect to the detection tasks.

304: The management apparatus detects detection task completion situations of at least two detection apparatuses and determines whether the number of uncompleted tasks is reduced to a preset proportion threshold of a total number of tasks; when the number of uncompleted tasks is reduced to the preset proportion threshold of the total number of tasks, executes step 305; otherwise, returns to step 304 to continue detection;

305: the management apparatus sends, to detection apparatuses that have not yet completed detection tasks, an instruction message to kill uncompleted detection tasks; executes step 306;

306: the detection apparatus judges whether a maximum interval of loci values in chromosome segments corresponding to the uncompleted detection tasks is greater than or equal to a preset loci interval; if yes, executes step 307; otherwise, when the maximum interval of loci values in chromosome segments corresponding to the uncompleted detection tasks is smaller than a preset loci interval, executes step 308;

307: the detection apparatus, according to the instruction message to kill the uncompleted detection tasks, kills the uncompleted detection tasks; executes step 309;

308: the detection apparatus does not kill uncompleted processes and monitors the process of structural variation detection of the detection task until the detection is completed; executes step 310;

309: the detection apparatus reports a listing of killed uncompleted detection tasks to the management apparatus; executing step 311;

310: the detection apparatus sends a detection result file of a corresponding detection task to the management apparatus; executes step 312;

311: the management apparatus considers killed uncompleted detection tasks as a new test sequence, and executes step 300;

That is to say, in the present embodiment, it is feasible to consider killed uncompleted detection tasks as a new test sequence for further division, and send the detection tasks to the detection apparatuses for further detection, that is, iteratively execute the above steps for the uncompleted detection tasks.

312: the management apparatus merges detection result files sent by the detection apparatus after completion of detection, as a detection result of the original test sequence.

According to the method of detecting structural variation in the present embodiment, with the technical solution being employed, the chromosome segment corresponding to the uncompleted detection tasks in each round of structural variation detection is considered as a segment of test sequence again to repeatedly and iteratively execute the above steps, to sufficiently use the computer resources, quicken the detection process of structural variations of the whole test sequence, shorten the detection duration of the structural variations of the whole test sequence, and improve the detection efficiency.

Figure 4:
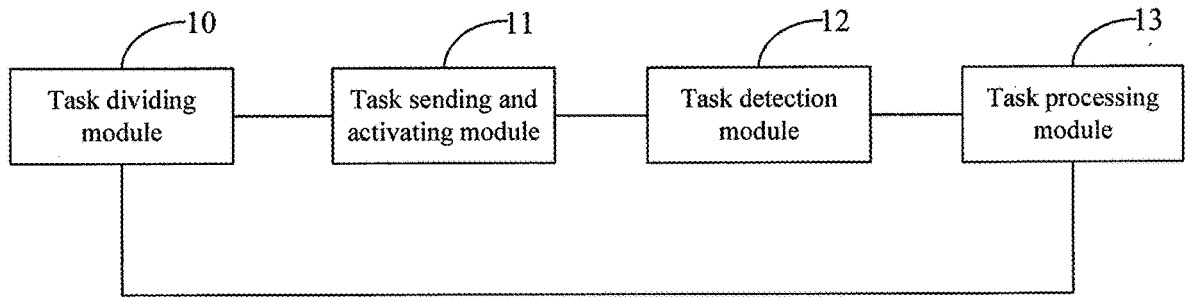
FIG. 4 is a structural diagram of an embodiment of a management apparatus for detecting structural variations according to the present disclosure.

FIG. 4 is a structural diagram of an embodiment of a management apparatus for detecting structural variations according to the present disclosure. As shown in FIG. 4, the management apparatus of detecting the structural variations in the present embodiment may specifically comprise: a task dividing module 10, a task sending and activating module 11, a task detection module 12 and a task processing module 13.

The task dividing module 10 is configured to divide a test sequence according to loci of chromosomes to obtain at least two portions of detection tasks; the task sending and activating modules 11 is configured to send respective detection tasks divided by the task dividing module 10 to respective detection apparatuses and activate the respective detection tasks; the task detection module 12 is configured to detect detection task completion situations of at least two detection apparatuses activated by the task sending and activating module 11 and determines whether the number of uncompleted tasks is reduced to a preset proportion threshold of a total number of tasks; the task processing module 13 is configured to, according to the detection result of the task detection module 12, send, to detection apparatuses that have not yet completed detection tasks, an instruction message to kill uncompleted detection tasks when the number of uncompleted tasks is reduced to the preset proportion threshold of the total number of tasks; the task dividing module 10 is further configured to divide the uncompleted detection tasks killed by the task processing module 13 into at least two portions; the task sending and activating module 11 is further configured to send respective detection tasks to respective detection apparatuses, and activate said respective detection apparatuses to continue to perform detection of structural variations.

As for the management apparatus for detecting structural variations in the present embodiment, an implementation principle of implementing structural variation detection by using the above modules and technical effects are identical with implementation of the relevant method embodiments. For details, reference may be made to the above relevant method embodiments, and no detailed depictions are presented here.

Further optionally, on the basis of the technical solution of the embodiment as shown in FIG. 4, the task dividing module 10 is specifically configured to divide the test sequence according to chromosomes; and divide all chromosomes after the division according to loci to obtain at least two portions of detection tasks.

Further optionally, on the basis of the technical solution of the embodiment as shown in FIG. 4, the task dividing module 10 is specifically configured in a way that according to the number of detection apparatuses included in the structural variation detection system and the number of cores of each detection apparatus, the management apparatus divides all chromosomes after the division according to loci to obtain at least two portions of detection tasks; and the portions of the at least two portions of detection tasks is equal to an integer multiple of a product of the number of detection apparatuses and the number of cores of each detection apparatus. This may ensure that each core processor of each detection apparatus may correspondingly process integer portions of detection tasks, and can ensure balance of resources, and shorten the overall detection duration, and improve the detection efficiency of the whole.

Further optionally, on the basis of the technical solution of the embodiment as shown in FIG. 4, the management apparatus further comprises: a receiving module configured to receive a listing of killed detection tasks which are sent by the detection apparatus.

Further optionally, on the basis of the technical solution of the embodiment as shown in FIG. 4, the management apparatus further comprises a merging module; the receiving module is further configured to receive a detection result file which is sent by each detection apparatus and with respect to a corresponding detection task when the detection tasks of detection apparatuses have been detected completed; the merging module is configured to merge the detection result files received by the receiving module.

Figure 5:
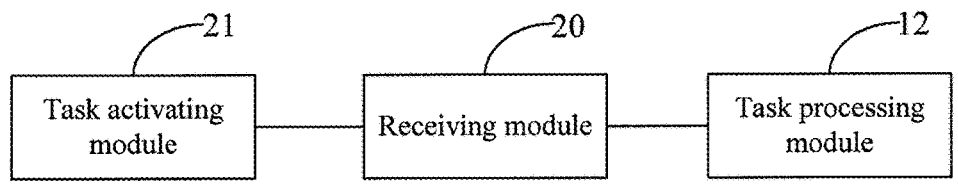
FIG. 5 is a structural diagram of an embodiment of a detection apparatus for detecting structural variations according to the present disclosure.

FIG. 5 is a structural diagram of an embodiment of a detection apparatus for detecting structural variations according to the present disclosure. As shown in FIG. 5, the detection apparatus for detecting structural variations according to the present embodiment specifically comprises: a receiving module 20, a task activating module 21 and a task processing module 22.

The receiving module 20 is configured to receive a detection task sent by a management apparatus; the receiving module 20 is further configured to receive an instruction message sent by the management apparatus to activate the detection task; the task activating module 21 is configured to, according to the instruction message received by the receiving module 20 to activate the detection task, simultaneously activates detection with respect to corresponding detection tasks together with other detection apparatuses; the receiving module 20 is further configured to, when the management apparatus detects that the number of uncompleted tasks is reduced to a preset proportion threshold of the total number of tasks, and when the current detection apparatuses have not completed the detection, receive an instruction message which is sent by the management apparatus and instructs to kill the uncompleted detection tasks; the task processing module 22 is configured to, according to the instruction message received by the receiving module 20 to kill the uncompleted detection tasks, kill the uncompleted detection tasks so that the management apparatus further divides the uncompleted detection task into at least two portions, sends respective detection tasks to respective detection apparatuses, and activates the detection apparatuses to continue to perform structural variation detection.

As for the detection apparatus for detecting structural variations in the present embodiment, an implementation principle of implementing structural variation detection by using the above modules and technical effects are identical with implementation of the relevant method embodiments. For details, reference may be made to the above relevant method embodiments, and no detailed depictions are presented here.

Further optionally, on the basis of the technical solution of the embodiment as shown in FIG. 5, the detection apparatus for detecting structural variations in the present embodiment further comprises a task detection module.

The task detection module is configured to judge whether a maximum interval of loci values in chromosome segments corresponding to the uncompleted detection tasks is greater than or equal to a preset loci interval; and determine that the maximum interval of loci values in chromosome segments corresponding to the uncompleted detection tasks is greater than or equal to the preset loci interval.

Further optionally, on the basis of the technical solution of the embodiment as shown in FIG. 5, the detection apparatus for detecting structural variations in the present embodiment further comprises a transmitting module.

The task processing module 22 is further configured not to kill uncompleted processes when the maximum interval of loci values in chromosome segments corresponding to the uncompleted detection tasks is smaller than the preset loci interval, and configured to monitor the process of structural variation detection of the detection task until the detection is completed;

The transmitting module is configured to transmit a detection result file of a corresponding detection task to the management apparatus.

Figure 6:
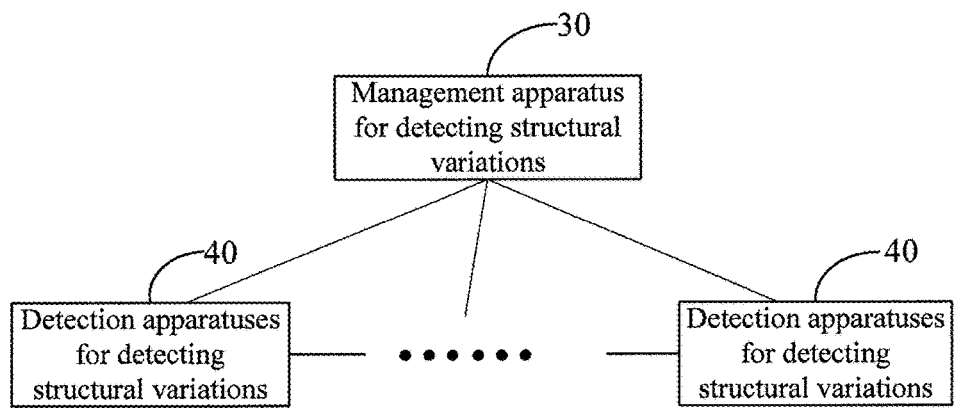
FIG. 6 is a structural diagram of an embodiment of a system for detecting structural variations according to the present disclosure.

FIG. 6 is a structural diagram of an embodiment of a system for detecting structural variations according to the present disclosure. As shown in FIG. 6, the system for detecting structural variations according to the present embodiment comprises: a management apparatus 30 for detecting structural variations and at least two detection apparatuses 40 for detecting structural variations. The management apparatus 30 for detecting structural variations is communicatively connected with the detection apparatuses 40 for detecting structural variations.

The management apparatus 30 for detecting structural variations according to the present embodiment employs the management apparatus for detecting structural variations of the embodiment as shown in FIG. 4; the detection apparatuses 40 for detecting structural variations employ the detection apparatuses for detecting structural variations in the embodiment as shown in FIG. 5. Specifically, it is feasible to employ the method of detecting the structural variations in embodiments as shown in FIG. 1-FIG. 3 to implement structural variation detection. For particulars, please refer to the depictions in the above relevant embodiments. In addition, in the present embodiment, when the number of the at least two detection apparatuses 40 for detecting structural variations is large to a certain degree, a detection cluster for detecting the structural variations may be formed, and the detection cluster is uniformly scheduled and controlled by the management apparatus 30 for detecting the structural variation.

In the embodiments provided by the present disclosure, it should be understood that the revealed system, apparatus and method can be implemented in other ways. For example, the above-described embodiments for the apparatus are only exemplary, e.g., the division of the units is merely logical one, and, in reality, they can be divided in other ways upon implementation.

The units described as separate parts may be or may not be physically separated, the parts shown as units may be or may not be physical units, i.e., they can be located in one place, or distributed in a plurality of network units. One can select some or all the units to achieve the purpose of the embodiment according to the actual needs.

Further, in the embodiments of the present disclosure, functional units can be integrated in one processing unit, or they can be separate physical presences; or two or more units can be integrated in one unit. The integrated unit described above can be implemented in the form of hardware, or they can be implemented with hardware plus software functional units.

The aforementioned integrated unit in the form of software function units may be stored in a computer readable storage medium. The aforementioned software function units are stored in a storage medium, including several instructions to instruct a computer apparatus (a personal computer, server, or network equipment, etc.) or processor to perform some steps of the method described in the various embodiments of the present disclosure. The aforementioned storage medium includes various media that may store program codes, such as U disk, removable hard disk, read-only memory (ROM), a random access memory (RAM), magnetic disk, or an optical disk.

What are stated above are only preferred embodiments of the present disclosure, not intended to limit the disclosure. Any modifications, equivalent replacements, improvements and the like made within the spirit and principles of the present disclosure, should all be included in the present disclosure within the scope of protection.

What is claimed is:

1. A method of detecting structural variations, the method comprising:
   dividing a test sequence data according to loci of chromosomes to obtain at least two portions of detection tasks;
   sending one of the at least two portions of detection tasks to each of at least two detection apparatuses respectively and activating the respective detection tasks;
   detecting detection task completion situations of the at least two detection apparatuses and determining whether the number of uncompleted tasks is reduced to a preset proportion threshold of a total number of tasks;
   when the number of uncompleted tasks is reduced to the preset proportion threshold of the total number of tasks, sending, to detection apparatuses that have not yet completed detection tasks, an instruction message to kill uncompleted detection tasks;
   further dividing the uncompleted detection tasks into at least two portions, sending one of respective detection tasks to each of respective detection apparatuses, and activating said respective detection apparatuses to continue to perform detection of structural variations.

2. The method according to claim 1, wherein the dividing a test sequence data according to loci of chromosomes to obtain at least two portions of detection tasks specifically comprises:
   dividing the test sequence according to chromosomes;
   dividing all chromosomes after the division according to loci to obtain at least two portions of detection tasks.

3. The method according to claim 2, wherein the dividing all chromosomes after the division according to loci to obtain at least two portions of detection tasks specifically comprises:
   according to the number of detection apparatuses included in the structural variation detection system and the number of cores of each detection apparatus, dividing all chromosomes after the division according to loci to obtain at least two portions of detection tasks; and the number of portions of the at least two portions of detection tasks is equal to an integer multiple of a product of the number of detection apparatuses and the number of cores of each computer.

4. The method according to claim 1, wherein when the number of uncompleted tasks is reduced to the original preset proportion threshold, and after sending to detection apparatuses that have not yet completed detection tasks, an instruction message to kill uncompleted detection tasks, the method further comprises:
   receiving a listing of killed detection tasks which are sent by the detection apparatus.

5. The method according to claim 1, wherein when detecting completion of detection tasks of respective detection apparatuses, the method further comprises:
   receiving a detection result file with respect to a corresponding detection task which is sent by each detection apparatus;
   merging the received detection result files.

6. An apparatus comprising
   one or more processors;
   a memory;
   one or more programs, which are stored in the memory, and execute the following operation when executed by the one or more processors:

dividing a test sequence data according to loci of chromosomes to obtain at least two portions of detection tasks;

sending one of the at least two portions of detection tasks to each of at least two detection apparatuses respectively and activating the respective detection tasks;

detecting detection task completion situations of the at least two detection apparatuses and determining whether the number of uncompleted tasks is reduced to a preset proportion threshold of a total number of tasks;

when the number of uncompleted tasks is reduced to the preset proportion threshold of the total number of tasks, sending, to detection apparatuses that have not yet completed detection tasks, an instruction message to kill uncompleted detection tasks;

further dividing the uncompleted detection tasks into at least two portions, sending one of respective detection tasks to each of respective detection apparatuses, and activating said respective detection apparatuses to continue to perform detection of structural variations.

7. The apparatus according to claim 6, wherein the operation of dividing a test data sequence according to loci of chromosomes to obtain at least two portions of detection tasks specifically comprises:

dividing the test sequence data according to chromosomes;

dividing all chromosomes after the division according to loci to obtain at least two portions of detection tasks.

8. The apparatus according to claim 7, wherein the operation of dividing all chromosomes after the division according to loci to obtain at least two portions of detection tasks specifically comprises:

according to the number of detection apparatuses included in the structural variation detection system and the number of cores of each detection apparatus, dividing all chromosomes after the division according to loci to obtain at least two portions of detection tasks; and the number of portions of the at least two portions of detection tasks is equal to an integer multiple of a product of the number of detection apparatuses and the number of cores of each computer.

9. The apparatus according to claim 6, wherein when the number of uncompleted tasks is reduced to the original preset proportion threshold, and after sending to detection apparatuses that have not yet completed detection tasks, an instruction message to kill uncompleted detection tasks, the operation further comprises:

receiving a listing of killed detection tasks which are sent by the detection apparatus.

10. The apparatus according to claim 6, wherein when detecting completion of detection tasks of respective detection apparatuses, the operation further comprises:

receiving a detection result file with respect to a corresponding detection task which is sent by each detection apparatus;

merging the received detection result files.

11. A non-transitory computer storage medium, encoded with programs, which, when executed by one or more computers, make the one or more computers to execute the following:

dividing a test sequence data according to loci of chromosomes to obtain at least two portions of detection tasks;

sending one of the at least two portions of detection tasks to each of at least two detection apparatuses respectively and activates the respective detection tasks;

detecting detection task completion situations of the at least two detection apparatuses and determines whether the number of uncompleted tasks is reduced to a preset proportion threshold of a total number of tasks;

when the number of uncompleted tasks is reduced to the preset proportion threshold of the total number of tasks, sending, to detection apparatuses that have not yet completed detection tasks, an instruction message to kill uncompleted detection tasks;

further dividing the uncompleted detection tasks into at least two portions, sending one of respective detection tasks to each of respective detection apparatuses, and activating said respective detection apparatuses to continue to perform detection of structural variations.

* * * * *